US006674529B2

United States Patent
Sachweh et al.

(10) Patent No.: US 6,674,529 B2
(45) Date of Patent: Jan. 6, 2004

(54) METHOD AND APPARATUS FOR DETERMINING PHYSICAL COLLECTIVE PARAMETERS OF PARTICLES OF GASES

(75) Inventors: Bernd Sachweh, Meckenheim (DE); Camiel Heffels, Gernsheim (DE); Matthias Rädle, Weisenheim am Berg (DE); Helmut Biermann, Bobenheim-Roxheim (DE); Hans Jürgen Eisen, Ludwigshafen (DE); Jürgen Ettmüller, Hassloch (DE); Johannes G Reuvers, Hohen-Sülzen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/915,308

(22) Filed: Jul. 27, 2001

(65) Prior Publication Data

US 2002/0018204 A1 Feb. 14, 2002

(30) Foreign Application Priority Data

Jul. 28, 2000 (DE) .......................... 100 36 860

(51) Int. Cl.⁷ .............................. G01N 21/00
(52) U.S. Cl. ....................... 356/338; 356/336
(58) Field of Search ................ 356/338, 340, 356/342, 336, 341, 343; 250/574, 573

(56) References Cited

U.S. PATENT DOCUMENTS

| 3,770,351 A | * | 11/1973 | Wyatt .......................... 356/336 |
| 4,529,306 A | | 7/1985 | Kilham et al. ........... 356/237.1 |
| 5,502,561 A | * | 3/1996 | Hutchins et al. ............ 356/336 |
| 6,055,052 A | * | 4/2000 | Lilifeld ........................ 356/338 |
| 6,288,783 B1 | * | 9/2001 | Auad .......................... 356/410 |

FOREIGN PATENT DOCUMENTS

AT          395270          11/1992

* cited by examiner

Primary Examiner—Hung Xuan Dang
Assistant Examiner—Tuyen Tra
(74) Attorney, Agent, or Firm—Keil & Weinkauf

(57) ABSTRACT

The present invention creates an apparatus for determining physical collective parameters of particles in gases, which comprises a measuring chamber with light entrance ports (121) and exit ports (123, 124) for electromagnetic radiation, an emission source (113) for electromagnetic radiation being provided and at least two detection apparatuses (114, 115) for determining the intensity of electromagnetic radiation scattered at the particles being provided, and the detection apparatuses (114, 115) detecting electromagnetic radiation of different scattering regions. The present invention further creates a method for determining physical collective parameters of particles in gases, the particles being exposed to electromagnetic radiation which is scattered at the particles, wherein the intensities of the scattered radiation of at least two different scattering regions are determined and their ratio is taken subsequently.

22 Claims, 2 Drawing Sheets

METHOD AND APPARATUS FOR DETERMINING PHYSICAL COLLECTIVE PARAMETERS OF PARTICLES OF GASES

BACKGROUND OF THE INVENTION

1. Field of the Invention

Gas streams, for example waste gas streams from chemical plants frequently contain vaporous components of substances foreign to air which lead to aerosol formation. Although as a rule the statutory limiting values for pollutants are met, the smoke plume associated with the aerosol formation is mostly troublesome. An intensified aerosol formation is frequently associated with specific malfunctions which can be precisely assigned and which it would be possible to assign even more precisely given precise knowledge of the aerosol quantity. The purely optically quantified aerosol quantity cannot always be determined absolutely with reference to the intensity of the smoke plume and is therefore problematical, since secondary effects such as, for example, the thinning of the aerosol in the ambient air, the vaporization of droplet aerosols, or the water vapor absorption of soluble, hygroscopic aerosols are superimposed. It is therefore difficult to undertake assignment of aerosol to operating states or malfunctions. The devising of countermeasures in the production area is therefore given over more or less to chance.

2. Description of the Related Art

Furthermore, aerosols in technical processes, in particular in plant combinations of large-scale chemical plants frequently lead to damage to catalysts, corrosion and product impurities. It has not so far been possible specifically to control the method processes with regard to avoiding aerosols or eliminating aerosols, since there is so far no safe, robust and reliable measuring technique. AT 395270 B discloses a method and an apparatus for absolute measurement of the numerical concentration of colloidal particles, in which an aerosol particle sample is supersaturated with vapor by adiabatic expansion in a measuring chamber, and this leads to uniform growth of the aerosol particles under consideration, their concentration subsequently being measured, by extinction of a coherent light beam penetrating the particle suspension concerned, simultaneously as a function of time with the light flux scattered at a predetermined angle.

A particular disadvantage of this method is that the aerosol particle sample to be investigated still has to be subjected before investigation to an adiabatic expansion for the purpose of supersaturation with vapor, and this is disadvantageous, in particular, for an online method.

It is known, furthermore, from U.S. Pat. No. 4,529,306 to monitor melted polymers for optical impurities by means of irradiation with preferably white light. In this case, a polymer, in particular a polymer melt is irradiated continuously by white light, and subsequently investigated for particles which refract white light by means of an optical detection unit. However, it is a disadvantage of this method that evaluation of the measurement results by image analysis can be applied starting only from particle sizes>50 micrometers.

It was therefore the object of the present invention to avoid the indicated disadvantages of the prior art and, in particular, to make available a method and an apparatus which render possible an objective evaluation of particle properties, in particular in gases.

This object is achieved by an apparatus with the characterizing features of the present invention, and by a method with the characterizing features of the present invention.

BRIEF SUMMARY OF THE INVENTION

Consequently, an apparatus according to the invention comprises a measuring chamber, preferably a flow-through cell, with entrance ports and exit ports for electromagnetic radiation, an emission source for electromagnetic radiation being provided and at least two detection apparatuses for determining the intensity of electromagnetic radiation scattered at the particles being provided, and the detection apparatuses detecting scattered electromagnetic radiation of different scattering regions.

It is therefore advantageously possible to apply the physical "multiangle scattering principle", in the case of which the sensitivity of the detection apparatus is adapted to specific particle size ranges by suitable selection of the detector positions which detect various scattering regions of the electromagnetic radiation.

Both gases which are at rest and those which are flowing are to be understood below under the term of gases for the purpose of their physical definition.

Physical collective parameters are to be understood below as, in particular, those properties and parameters of particles which are measured only as a mean value of the particle collective. Examples of this are concentration, mean particle diameter and the like.

It is understood by detection apparatus that this apparatus is suitable for detecting electromagnetic radiation and subsequently outputting an at least relative value of the electromagnetic radiation.

A first detection apparatus preferably detects scattered electromagnetic radiation from the forwardly scattered region (forward scattering). It is further preferred that a second detection apparatus detects scattered electromagnetic radiation from the backwardly scattered region (backscattering). It is thereby advantageously possible for aerosols with particle sizes of less than 10 $\mu$m in general to be detected with particular precision by suitable selection of the detector position in the two previously mentioned regions. This also holds in the case of simultaneous occurrence of particles with particle sizes of more than 10 $\mu$m in these gases.

In a particularly preferred embodiment, the forwardly scattered region comprises a forward scattering angle from 20 to 80° and the backwardly scattered region comprises a backscattering angle from 100 to 160°, as a result of which the sensitivity to aerosols with a particle size of less than 10 $\mu$m, in particular less than 5 $\mu$m, can be detected with particular preference.

It is further preferred that means are provided for determining the ratio of the scattering intensities of the forward scattering and backscattering. This permits the mean particle size of the aerosol particles to be determined by simply bringing the two values into a relationship with one another. It is thereby preferably possible to detect mean particle sizes to 0.1 $\mu$m. Particles with sizes above 10 $\mu$m do not interfere in this case.

In a further preferred embodiment, means are provided for purging the emission source for electromagnetic radiation and/or for the detection apparatuses with at least one fluid. Purging with a fluid prevents a deposition of very fine particles on the optical system from leading to false measured values after a short operating time.

It is further preferred that means for multistage or continuous purging are provided. This ensures that even after a single purging very fine deposited particles still present are removed in a simple way from the optical system of the emission source of electromagnetic radiation and/or from the detection apparatuses, or that the deposits are prevented.

In a further preferred embodiment, it is provided that different fluids are provided for each purging stage. It is thereby preferably possible, for example, that a first purging is performed with air and very fine particles not removed and which would not longer be removable when dry are purged in a second purging with a liquid, for example water. Air is used again for purging in the third purging stage, with the result that after the liquid purging the optical apparatus is preferably blown dry by the purging line, thus excluding erroneous measurement owing to the deposition of drops of the purging liquid on the optical system.

In a further preferred embodiment, a third detection apparatus is provided which, for example, detects radiation with a mean scattering angle of 0°.

In addition to the simple detection, previously outlined, of aerosol particles of $\leq 10$ $\mu$m, it is thereby simultaneously possible to measure particles in the gas which have a size of more than 10 $\mu$m, for example drops and dust. This measuring apparatus also permits precise differentiation between fine and coarse particles in a gas, and their simultaneous detection.

The emission source for electromagnetic radiation preferably emits wavelengths in the region of white visible light, ambiguity being avoided, in particular, in the determination of the particle size.

In a further preferred embodiment, means are provided for limiting the optically defined measurement volume, something which depresses the lower detection limits with reference to particle size and/or particle concentration owing to a higher radiation intensity in the measurement volume.

The above-named object of the present invention is achieved, furthermore, by a method according to the present invention.

It is provided thereby that the intensities of the scattered radiation of at least two different scattering regions are determined and their ratio is taken subsequently.

This advantageously permits simple determination of particle size, in particular in the range of $\leq 10$ $\mu$m.

In an advantageous embodiment, one scattering region comprises the forwardly scattered region, and the other scattering region comprises the backscattered region. It is further preferred that the forward scattering angle comprises 20 to 80° and the backscattering angle comprises 100 to 160°, since thereby the sensitivity of the detection apparatus can advantageously be set to specific particle size ranges of less than 10 $\mu$m.

In the method according to the invention, the intensity of the scattered radiation in a third scattering region is preferably measured, with particular preference for a mean scattering angle of 0°. The method according to the invention thereby makes available in a simple way the determination of particle sizes within the overall particle size range in gases, thereby rendering it possible simultaneously to measure and analyze in a simple way aerosols and also large particles in a gas.

The electromagnetic radiation preferably comprises wavelengths in the region of visible white light, since it is thereby possible in a simple way to avoid ambiguities in the determination of the particle size.

The method according to the invention is preferably used to determine physical properties of aerosols in gases which additionally contain particles which have particle sizes of more than 10 $\mu$m.

Further advantages and refinements follow from the description and the attached drawings.

It goes without saying that the aforementioned features and those still to be explained below can be used not only in the combination respectively specified, but also in other combinations, or on their own, without leaving the scope of the present invention.

The invention is illustrated schematically in the drawings with the aid of two exemplary embodiments, and is described in detail below with reference to the drawings, in which:

DETAILED DESCRIPTION OF THE INVENTION

Figure 1:
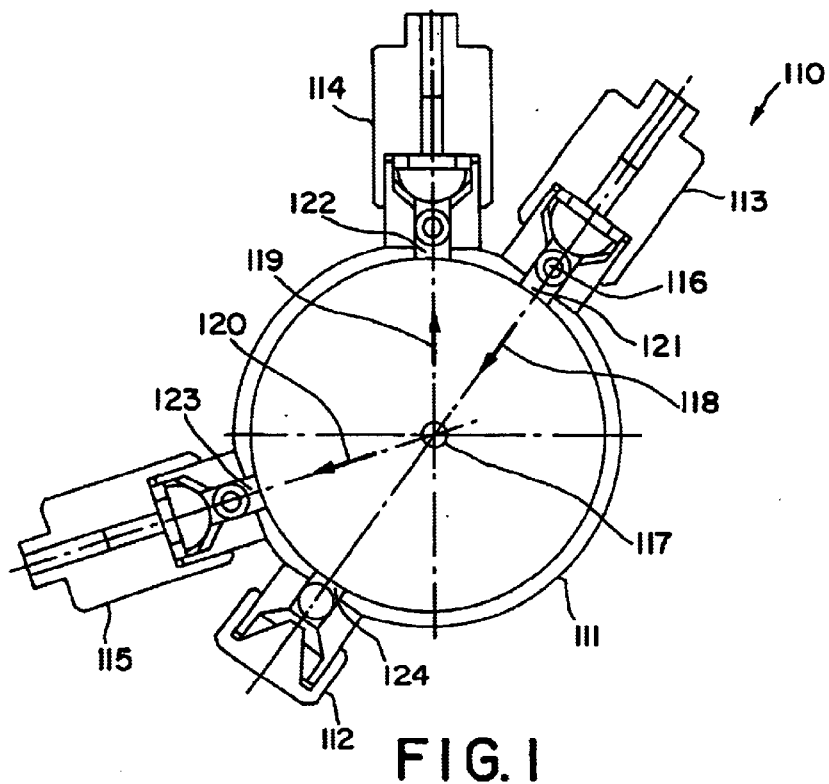
FIG. 1 shows an embodiment of an apparatus according to the invention.

A schematic cross section through an apparatus (110) according to the invention is illustrated in FIG. 1. Said apparatus therefore comprises a measurement chamber (111) known per se, at which there are provided ports (121, 122, 123 and 124) which permit the entry or exit of electromagnetic radiation. The port (125) is closed in the present exemplary embodiment and cannot be penetrated by electromagnetic radiation.

A source of electromagnetic radiation which is known to the person skilled in the art and denoted below as emission source (113) is fitted at a first port (121). The emission source (113) can preferably emit white light in the visible region, in this case, but other wavelengths such as those in the laser, LED, NIR, UV regions and the like are also conceivable. The typical edge length of the optically defined measurement volume in the stream should not exceed 10 mm for technical reasons relating to application. This is achieved by the installation of a suitable focusing optical system in the emission source (113) and/or in the detectors. On the opposite side of the measurement chamber with reference to the emission source (113), a light trap (112) is fitted at a second port (124) and absorbs and dissipates the emerging light.

Fitted adjacent to the emission source (113) is a first detection apparatus (114) for detecting the backwardly scattered light. This is arranged at the port (122). The backscattering angle is preferably from 100 to 160°, preferably 110 to 150°. The optimum angular range is achieved by arranging the detection apparatus (114) in a fashion respectively adapted to the conditions, and is also a function of the aerosol respectively to be determined. In the region of the forwardly scattered light, a second detection apparatus (115) is arranged at a third port (123) for the purpose of determining the forwardly scattered light. The forward scattering angle is in this case from 20 to 80°, preferably from 30 to 70°. These two detection apparatuses (114 and 115) in this case advantageously permit the application of the multiangle scattering principle, in which scattered light from particle collectives can be detected from the forward and backward scattering regions. The particle size to be determined can be set precisely by precisely setting the position of the two detection apparatuses (114 and 115). Large particles and particle sizes of greater than 10 μm, for example drops and dust, which are contained in the gas stream have no relevant influence on the measurement result in this arrangement of the scattering angles.

A purging apparatus (116) for purging the optical apparatus (optical system) of the emission source (113) and/or detectors (114, 115) with compressed air or a liquid can also be arranged at the emission source (113). It is likewise possible by suitable interconnection that the air purging usually employed can be replaced by multistage purging with air, liquid and compressed air via the purging lines, it being possible owing to the purging with air downstream of the liquid purging for the optical system to be blown dry, erroneous measurements owing to deposits of drops of the purging liquid on the optical system being excluded. However, it is likewise possible to purge the optical system of the emission source (113) only with air or with liquid or another fluid in a single-stage purging variant.

A particle (117) is shown schematically in the measuring chamber (111) in FIG. 1. Of course, a plurality of particles are present in a gas in an apparatus according to the invention; this fact is ignored, with a view to simplifying the principle in FIG. 1.

The emission source (113) emits electromagnetic radiation, preferably in the visible region of light, which is illustrated by the arrow (118). This radiation is scattered at the particle (117). The scattering in the region of the backwardly scattered light is illustrated by the arrow (119), which is detected by the first detection apparatus (114). The scattered radiation in the region of the forwardly scattered light is illustrated by the arrow (120) and detected by the second detection apparatus (115). Means (not illustrated in FIG. 1) for taking the ratio of the intensities of forwardly scattered and backscattered light permit the determination of the mean particle size of the aerosol particles. The absolute level of the scattered light intensity, which can be measured either in forward scattering or backscattering or else, however, in a combination of the two, preferably in the forward direction, in particular, is used to determine the numerical concentration. The lower limit for the particle size is at 0.1 μm, and the minimum measurable mass concentration is approximately 0.1 mg/m$^3$.

Fiber-optic sensors, which can be used in areas subject to explosion hazards and in the presence of electromagnetic fields, are preferably used to detect the scattered light in the detection apparatuses (114 and 115) and/or the emission source (113).

Figure 2:
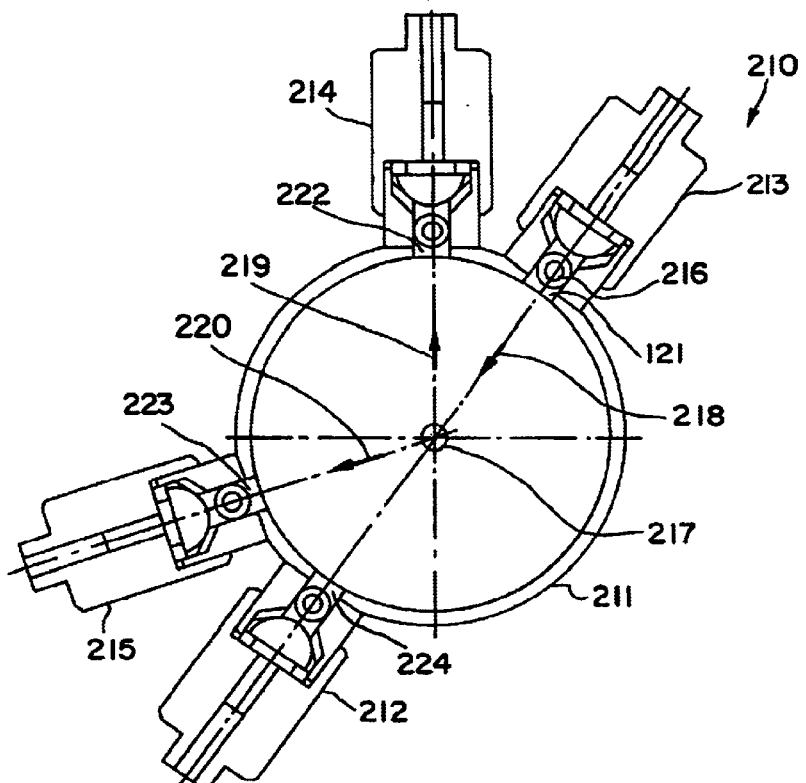
FIG. 2 shows a further embodiment of an apparatus according to the invention.

A further embodiment of the apparatus according to the invention is illustrated in FIG. 2. The apparatus (210) according to the invention in FIG. 2 is designed essentially by analogy with the apparatus in FIG. 1. A particle (217) is located in a measuring chamber (211) for the purpose of illustrating the measuring principle according to the invention by way of example. Furthermore, ports (221, 222, 223 and 224) for the entry and exit of electromagnetic radiation are provided at the measuring chamber (211).

An emission source (213) with a purging apparatus (216) illustrated in FIG. 1 is arranged at the port (221). Arranged next to the source (213) is a first detection apparatus (214) at the port (222) for detecting the backwardly scattered radiation, illustrated by an arrow (219).

Provided in the region of the forwardly scattered radiation at the port (223) is a second detection apparatus (215) for detecting the forwardly scattered light, illustrated by the arrow (220). Opposite the emission source (213), which emits electromagnetic radiation illustrated by the arrow (218), a third detection apparatus (212) is arranged at the port (224) and detects attenuated light which strikes the third detection apparatus (212) with a mean scattering angle of 0°. This is a variant of the extinction measurement, the light attenuation being measured by all the particles present in the gas stream. This measuring method is also known as the photometric measuring technique and can, however be used only in the range of mean particle sizes above 10 μm. Consequently, the apparatus (210) illustrated in FIG. 2 can be used to measure particles in the range of less than 10 μm, known as aerosols, and also particles with a mean size of more than 10 μm which occur in what is termed the coarse dust range, for example drops and dusts. The apparatus in FIG. 2 thus permits simultaneous measurement of all particle sizes occuring in a gas.

The principles, illustrated in FIG. 1, for the detection apparatus and for the optically defined measurement volume also hold in FIG. 2. The purging of the emission source (213) and/or the detection apparatuses (214, 215, 212) by means of the purging apparatus (216) is likewise performed in accordance with the principles explained in FIG. 1.

Figure 3:
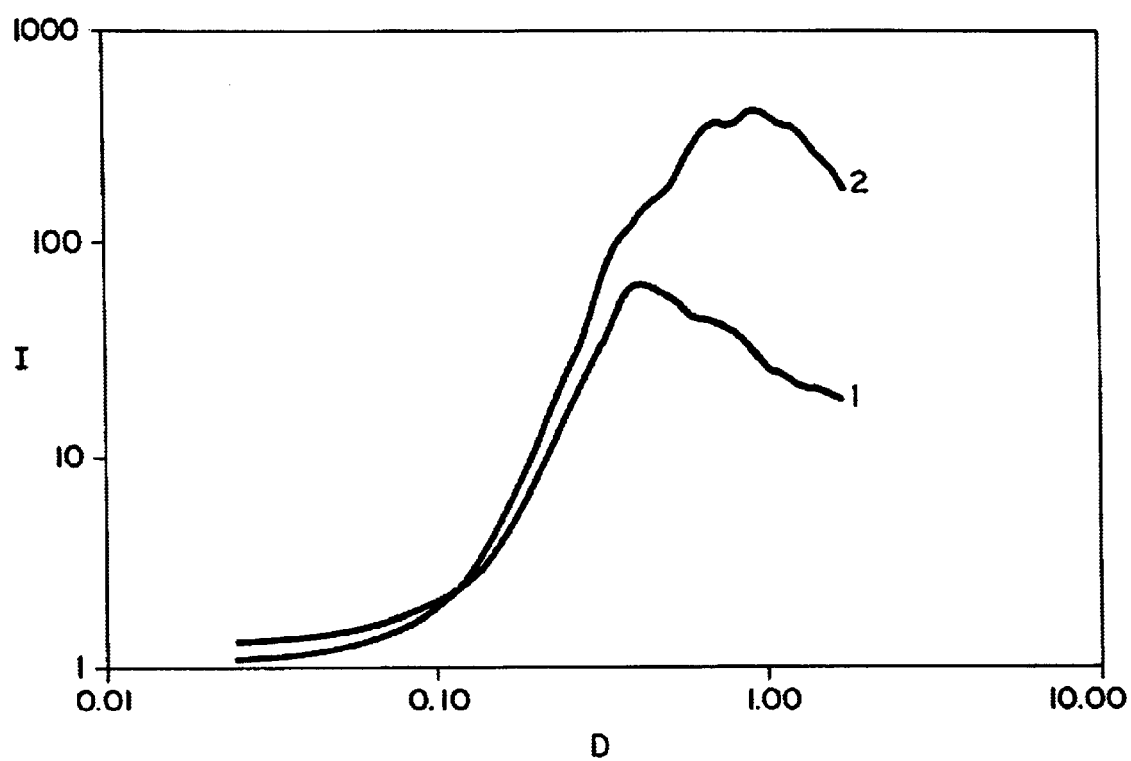
FIG. 3 shows the intensity ratio of the scattered electromagnetic radiation as a function of particle size for various arrangements of the detection apparatus in the respective scattering regions.

FIG. 3 shows the intensity ratio (I) of the forwardly and backwardly scattered light as a function of the particle size in μm (D) and of the ranges for the forward scattering and backscattering angles.

Curve 1 shows the intensity ratio of a forward scattering angle of 40° and a backscattering angle of 120°. As may be seen, it is possible on the falling branch of curve 1 to measure, in particular, particles with diameters in the range from 0.4 to 5 μm with particular accuracy when no particles are present with a diameter of less than 0.4 μm.

Curve 2 has the intensity ratio of a forward scattering angle of 20° and a backscattering angle of 160°. Particle sizes from 0.1 to 1 μm, in particular, can be determined thereby.

As emerges from FIG. 3, the arrangements, on which curves 1 and 2 are based, for the spatial arrangement of the detection apparatus for forwardly and backwardly scattered radiation are suitable for measuring aerosols which have precisely a particularly small particle range of, in particular, <5 μm, preferably from 0.1 to 5 μm. Virtually all the technically relevant aerosols which can occur, in particular, during operation, for example in the waste gas from chemical plants, are found precisely in this size range.

An apparatus and the method according to the invention are used, for example, in the field of combined chemical plants where a successful reduction in aerosols is rendered possible, for example in the field of fertilizer production. Further possibilities of use are, for example, the continuous monitoring of flue gases, the detection of condensation nuclei in cyclic gas processes or the monitoring of filter bags.

The invention also relates to a computer program with program coding means for carrying out the method according to the invention or for carrying it out with the aid of the apparatus according to the invention, and appropriate data media with these computer programs.

We claim:

1. An apparatus for determining physical collective parameters of particles in waste gas streams from chemical plants, which comprises a measuring chamber with entrance ports and exit ports for electromagnetic radiation, an emission source for electromagnetic radiation being provided and at least two detection apparatuses for determining the intensity of electromagnetic radiation scattered at the particles being provided, and the detection apparatuses detecting scattered electromagnetic radiation of different scattering regions, wherein means for multistage or continuous purging of the emission source for electromagnetic radiation with at least one fluid provided.

2. An apparatus as claimed in claim 1, wherein a first detection apparatus detects scattered electromagnetic radiation from the forwardly scattered region.

3. An apparatus as claimed in claim 2, wherein the forwardly scattered region comprises a forward scattering angle from 20° to 80°.

4. An apparatus as claimed in claim 1, wherein a second detection apparatus detects scattered electromagnetic radiation on the backwardly scattered region.

5. An apparatus as claimed in claim 4, wherein the backwardly scattered region comprises a backscattering angle from 100° to 160°.

6. An apparatus as claimed in claim 1, wherein means are provided for determining the ratio of the scattering intensities of the forward scattering and backscattering.

7. An apparatus as claimed in claim 6, wherein a third detection apparatus is provided.

8. An apparatus as claimed in claim 7, wherein the third detection apparatus detects radiation with a mean scattering angle of 0°.

9. An apparatus as claimed in claim 1, wherein means for purging in the detection apparatuses for electromagnetic radiation are provided with at least one fluid.

10. An apparatus as claimed in claim 1, wherein different fluids are used for purging in each stage.

11. An apparatus as claimed in claim 1, wherein the emission source for electromagnetic radiation emits wavelengths in the region of visible light.

12. An apparatus as claimed in claim 1, wherein means are provided for limiting an optically defined measurement volume.

13. A computer program with program coding means for running with the aid of the apparatus in accordance with claim 1.

14. A method for determining physical collective parameters of particles in waste gas streams from chemical plants, the particles being exposed to electromagnetic radiation emitted by an emission source, said electromagnetic radiation being scattered at the particles, wherein the intensities of the scattered radiation of at least two different scattering regions are determined and their ratio is subsequently taken and wherein the emission source is purged continuously or in a multistage process with at least one fluid.

15. A method as claimed in claim 14, wherein one scattering region comprises the forwardly scattered region, and the other scattering region comprises the backscattered region.

16. A method as claimed in claim 15, wherein the forwardly scattered region comprises a forward scattering angle from 20° to 80°, and the backwardly scattered region comprises a backscattering angle from 100° to 160°.

17. A method as claimed in claim 14, wherein the intensity of the scattered radiation in a third scattering region is measured.

18. A method as claimed in claim 17, wherein the third scattering region has a mean scattering angle of 0°.

19. A method as claimed in claim 14, the electromagnetic radiation comprising wavelengths in the region of visible light.

20. The method as claimed in claim 14 for determining aerosols in gases which contain particles which have mean particle sizes of more than 10 $\mu$m.

21. A computer program with program coding means for carrying out the method in accordance with claim 14.

22. A data medium with a computer program as claimed in claim 21.

* * * * *

UNITED STATES PATENT AND TRADEMARK OFFICE
CERTIFICATE OF CORRECTION

PATENT NO.     : 6,674,529 B2
DATED          : January 6, 2004
INVENTOR(S)    : Sachweh et al.

It is certified that error appears in the above-identified patent and that said Letters Patent is hereby corrected as shown below:

Column 6,
Line 63, after "chamber" insert -- through which a waste gas stream flows, --.

Signed and Sealed this

Eleventh Day of May, 2004

JON W. DUDAS
*Acting Director of the United States Patent and Trademark Office*